United States Patent [19]
Greenhaff et al.

[11] Patent Number: 6,143,784
[45] Date of Patent: Nov. 7, 2000

[54] REDUCING MUSCLE FATIGUE

[75] Inventors: Paul Leonard Greenhaff; Elizabeth Jane Simpson; Dumitru Constantin-Teodosiu, all of Nottingham, United Kingdom

[73] Assignee: The University of Nottingham, United Kingdom

[21] Appl. No.: 09/200,308

[22] Filed: Nov. 25, 1998

[30] Foreign Application Priority Data

Nov. 25, 1997 [GB] United Kingdom ............... 9724813

[51] Int. Cl.⁷ .................................... A61K 31/22
[52] U.S. Cl. ................................. 514/546; 514/557
[58] Field of Search .......................... 514/546, 557

[56] References Cited

FOREIGN PATENT DOCUMENTS 353 065   1/1990   European Pat. Off. .

OTHER PUBLICATIONS

*Metabolic responses from rest to steady state determine contracile function in ischemic skeletal muscle*, Jack A. Timmons, et al., American Physiological Society, pp. E233–238, 1997.

*Maximum Rate of Oxygen uptake by humas skeletal muscle in relation to maximal activities of enzymers in the Krebs Cycle*, Eva Blomstrand et al., Journal of Physiology (1997) pp. 455–460.

*Tricarboxylic acid cycle intermediates in human muscle during prolonged exercise*, K Sahlin et al., The American Physiological Society, 1990, pp. C835–C841.

*Primary Examiner*—Rebecca Cook
*Attorney, Agent, or Firm*—Watts Hoffmann Fisher & Heinke Co LPA

[57] ABSTRACT

A method of reducing muscle fatigue during exercise or for treating chronic heart failure, the method comprising increasing the concentration of TCA cycle intermediates in the muscle mitochondria by the administration of pyruvate to the body.

10 Claims, No Drawings

REDUCING MUSCLE FATIGUE

The present invention relates to muscle fatigue and particularly but not exclusively to a method for reducing muscle fatigue in humans.

Pyruvate is known to be present in the muscles of vertebrates. It is produced naturally in the body by glycolysis in the cytosol of cells. During aerobic exercise the pyruvate can be completely oxidised through the Tricarboxylic acid cycle (TCA cycle) in mitochondria. During prolonged exercise the muscle pool of TCA cycle intermediates can become deleted which has been suggested to reduce the rate of the cycle and hence reduce the rate at which the muscle produces energy, which may result in fatigue.

It has recently been demonstrated that there is a lag in the activation of mitochondrial energy production in the muscle at the beginning of exercise, in which instance muscle will use anaerobic systems such as converting pyruvate to lactate to compensate for the energy deficit. This can lead to the muscle activity being impaired and can result in muscle fatigue. Similarly, during more prolonged exercise mitochondrial respiration has been suggested to be comprised, resulting in fatigue (Sahlinstal 1990).

It has been suggested that the lag in mitochondrial respiration at the onset of exercise may reside at the level of the TCA. Further, during prolonged exercised, that depletion of TCA cycle intermediates may limit mitochondrial energy production.

According to the present invention there is provided a method of reducing muscle fatigue during exercise, the method comprising increasing the concentration of TCA cycle intermediates in the muscle mitochondria by the administration of pyruvate to the body.

The TCA cycle intermediates concentration may be increased by ingestion and/or infusion of pyruvate.

The pyruvate is preferably orally ingested. The pyruvate may be in the form of a powder, tablet or sustained release capsule. The pyruvate powder may be made into solution prior to administration.

The pyruvate may be administered prior to and/or during exercise.

The pyruvate may be in the form of a dietary supplement.

The invention also provides the use of pyruvate for the treatment of skeletal muscle vascular insufficiency.

The invention also provides the use of pyruvate for the treatment of chronic heart failure.

The pyruvate is preferably intravenously infused.

The invention also provides the use of pyruvate for the manufacture of a medicament for the treatment of skeletal muscle vascular insufficiency.

The invention also provides the use of pyruvate for the manufacture of a medicament for the treatment of chronic heart failure.

Preferably the pyruvate is synthesised from bacteria.

The invention will be further described for the purposes of illustration only with reference to the following example.

Six men were intravenously infused for 30 minutes with a pyruvate solution at a rate of 1.67 mg.kgbody mass$^{-1}$.min$^{-1}$. Muscle biopsy samples, obtained from the vastus lateralis immediately before and after each infusion, were analysed for the concentration of pyruvate dehydrogenase complex (PDC), and pyruvate metabolites such as TCA cycle intermediates, in skeletal muscle. The results are shown in the following table.

|  | Pyruvate | |
|---|---|---|
|  | Pre | Post |
| PDCa[1] | 0.36 ± 0.05 | 0.35 ± 0.10 |
| Pyruvate[2] | 0.18 ± 0.02 | 0.26 ± 0.07 |
| Lactate[2] | 4.31 ± 0.74 | 4.82 ± 0.62 |
| Acetylcarnitine[2] | 2.78 ± 0.53 | 1.97 ± 0.26 |
| Citrate[2] | 0.34 ± 0.01 | 0.38 ± 0.04 |
| Malate[2] | 0.24 ± 0.03 | 0.41 ± 0.05 |
| 2-oxoglutarate[2] | 0.07 ± 0.02 | 0.08 ± 0.01 |
| ETCAP | 0.66 ± 0.02 | 0.89 ± 0.09 |

Values represent mean ± SEM.
[1]mmol min$^{-1}$ kg$^{-1}$ wet mass;
[2]mmol kg$^{-1}$ dry mass These results demonstrate that pyruvate infusion significantly increased the concentration of TCA cycle intermediates (TCAI), probably by providing a readily available supply of pyruvate for anaplerosis i.e. conversion of pyruvate into TCA cycle intermediates such as oxaloacetate, malate, and α keto glutarate.

Whilst in the above example the pyruvate is infused, in other situations the pyruvate could be ingested. The pyruvate could be ingested in the form of a tablet, sustained release capsule, or powder. In the latter case the powder could be dissolved prior to ingestion. The pyruvate could be administered prior to or during exercise. For example, a pyruvate solution could be used by cyclists in drink bottles whilst cycling.

At the beginning of exercise, there may be a lag in mitochondrial ATP production which resides at the level of the TCA cycle. Accordingly, the mitochondria may depend to at least some degree on anaerobic systems for producing energy, which may result in muscle fatigue. Administering pyruvate prior to exercise will increase the concentration of TCA cycle intermediates in the mitochondria, and thus reduce the requirement for anaerobic systems to produce energy.

The concentration of the TCA cycle intermediates may be depleted during prolonged exercise which may limit mitochondrial ATP production and result in fatigue. This can be remedied by the taking in of pyruvate. This replenishing of intermediates could result in the possibility of exercising for longer periods.

Pyruvate could also be used to treat skeletal muscle vascular insufficiency or chronic heart failure. The invention also covers the preparation of a medicament including pyruvate for treating such disorders.

Other modifications may be made within the scope of this invention. The pyruvate may be synthesised artificially or from bacteria.

Whilst endeavouring in the foregoing Specification to draw attention to those features of the invention believed to be of particular importance it should be understood that the Applicant claims protection in respect of any patentable feature hereinbefore referred to whether or not particular emphasis has been placed thereon.

What is claimed is:

1. A method of reducing muscle fatigue in a mammal during exercise, the method comprising administering to said mammal, an effective amount of pyruvate to increase a concentration of tricarboxylic acid cycle intermediates in a muscle mitochondrea of said mammal.

2. A method according to claim 1, wherein the tricarboxylic acid cycle intermediates concentration is increased by oral ingestion of pyruvate.

3. A method according to claim 2, wherein the pyruvate is in the form of a powder.

4. A method according to claim 2, wherein the pyruvate is in the form of a tablet.

5. A method according to claim 2, wherein the pyruvate is in the form of a sustained release capsule.

6. A method according to claim 1, wherein the pyruvate powder is made into solution prior to administration.

7. A method according to claim 1, wherein the tricarboxylic acid cycle intermediates concentration is increased by infusion of pyruvate.

8. A method according to claim 1, wherein the pyruvate is administered prior to exercise.

9. A method according to claim 1, wherein the pyruvate is administered during exercise.

10. A method according to claim 2, wherein the pyruvate is in the form of a dietary supplement.

* * * * *